United States Patent [19]

Hirai et al.

[11] 4,418,058
[45] Nov. 29, 1983

[54] PROTECTION OF LYOPHILIZED BETALACTAMS FROM COLOR FORMATION

[75] Inventors: Eizo Hirai, Kawanishi; Kazuhiro Shima, Yamatokoriyama, both of Japan

[73] Assignee: Shionogi & Co., Ltd., Osaka, Japan

[21] Appl. No.: 272,895

[22] Filed: Jun. 12, 1981

[30] Foreign Application Priority Data

Jun. 23, 1980 [JP] Japan ............................ 55-85789

[51] Int. Cl.³ .................... A61K 31/00; A61K 47/00; A61K 31/535
[52] U.S. Cl. ........................................... 424/176
[58] Field of Search ............ 424/176, 248.5, 248.51; 544/90

[56] References Cited

U.S. PATENT DOCUMENTS 3,993,753 11/1976 Batal .................................. 424/176
4,180,571 12/1979 Narisada et al. ............... 424/248.52

Primary Examiner—Albert T. Meyers
Assistant Examiner—John W. Rollins, Jr.
Attorney, Agent, or Firm—Wenderoth, Lind & Ponack

[57] ABSTRACT

A stable preparation of a lyophilized β-lactam antibacterial containing a 7β-(α-carboxy-α-arylacetamido)-7α-methoxy-3-heterocyclic thiomethyl-1-dethia-1-oxa-3-cephem-4-carboxylic acid (I) alkali metal salt as the antibacterial component and a sugar or sugar alcohol compound as the stabilizing agent.

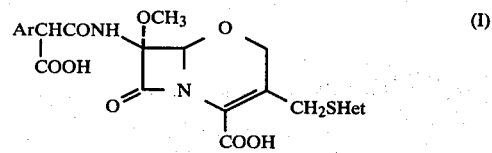

(wherein
Ar is a p-hydroxyaryl group and
Het is a heterocyclic group optionally substituted by an alkyl group)

27 Claims, 2 Drawing Figures

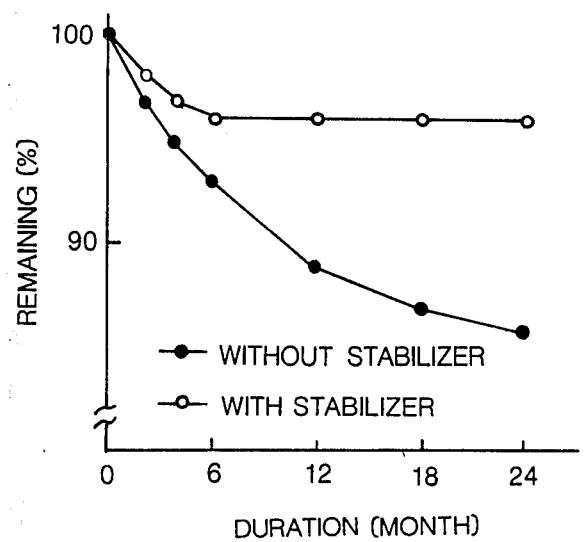
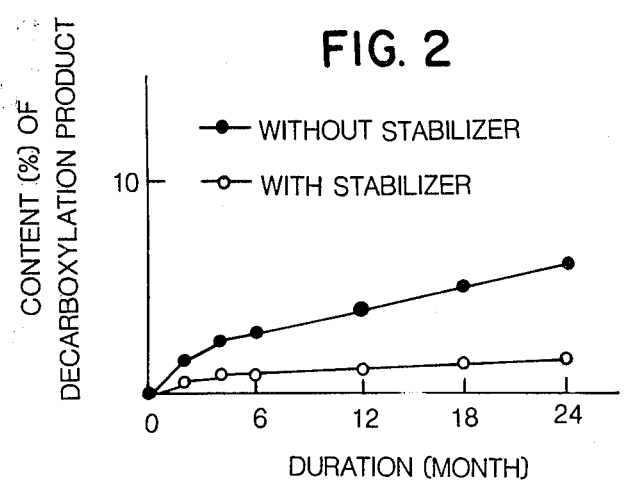

PROTECTION OF LYOPHILIZED BETALACTAMS FROM COLOR FORMATION

This invention relates to a stable preparation of lyophilized beta-lactam antibacterial containing a 7β-(α-carboxy-α-arylacetamido)-7α-methoxy-3-heterocyclic thiomethyl-1-dethia-1-oxa-3-cephem-4-carboxylic acid (I) alkali metal salt as the antibacterial component and a sugar or sugar alcohol compound as the stabilizing agent mainly for the purpose of preventing blue color formation.

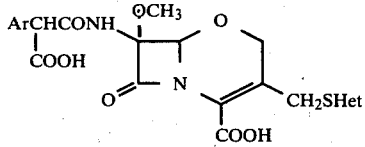

(wherein Ar is a p-hydroxyaryl group and

Het is a heterocyclic group optionally substituted by an alkyl group)

A lyophilized preparation consisting of an alkali metal salt of the compound (I) gets significant deep blue-violet color after storage for 2 months at room temperature or after 2 days at 40° C. This phenomenon requires existence of p-hydroxyaryl, side chain carboxylate, 7α-methoxy- and 3-heterocyclic thiomethyl as necessary structures. Sometimes, the preparation gets light and distinct yellowish color in addition. Moreover, other decompositions, e.g. carbon dioxide elimination from the side chain carboxylate group the decreasing antibacterial activity, are usually observable. To prevent such deteriorations, some sugar and sugar alcohol compounds are now found effective.

In the above formula (I), the Ar group is an aryl group having a hydroxy group at the para-position and optionally having halogen, hydroxy, lower alkoxy, lower alkyl or the like. Here, lower means those having preferably 1C to 3C. Typical is p-hydroxyphenyl and halo-p-hydroxyphenyl.

The Het group is a heterocyclic group, e.g. five or six membered monocyclic group, and preferably having 3 or 4 heteroatoms selected from nitrogen, sulfur and oxygen in its nucleus. Representative are tetrazolyl, thiadiazolyl, triazolyl, triazinyl and the like groups, each optionally substituted by an alkyl substituent e.g. lower alkyl preferably having 1 to 5 carbon atoms exemplified by methyl, ethyl, isobutyl or the like.

The alkali metal salt may be a lithium, sodium or potassium salt. This can be a mono-salt or di-salt, or mixtures thereof.

Some sugar and sugar alcohol compounds have now been found to prevent said color formation. The sugar alcohol compounds contain usually 4 to 8 carbon atoms, especially six carbon atoms e.g. arabitol, dambonitol, dulcitol, inositols, mannitol, ononitol, pinitol, quercitol, sequoytol sorbitol, viburnitol, xylitol, cyclohexanepentols and the like. The sugar compounds and mono- or disaccharide e.g. allose, altrose, arabinose, fructose, galactose, glucose, gulose, idose, lactose, lyxose, maltose, mannose, ribose, ribulose, sedoheptulose, sorbose, sucrose, tagatose, talose, xylose, and the like.

Among these, physiologically inactive mannitol is the most effective and clinically suitable to avoid excessive effects on the body of subjects to be administered. For example, glucose is as effective as mannitol, but has the defects of being a nutrient and of raising the blood sugar level. Thus, mannitol supercedes glucose.

The compounds (I) and their salts are potent antibacterials disclosed in e.g. Japanese published patent application Kohai Nos. 52-133997, 53-84987, 54-19990, 36287.

The compounds (I) in an alkali metal salt form usually crystallize only with difficulty and have been served as a lyophilized product for the purpose of storage or supply for clinical use. However, after storing for a period of a few weeks or under an accelerating condition, long lasting dark blue-violet color develops, sometimes accompanied by yellowish gray color.

From the chemical aspects, carbon dioxide elimination from the side chain carboxylate group is found and confirmed by isolating the corresponding decarboxylated compound. From the decomposed mixture after storage over the aforementioned period, the corresponding heterocyclic thiol compound is also detectable by high precision liquid chromatography to show some decompositions.

Antibacterial potency of lyophilized preparations falls down remarkably from the initial value when none of the stabilizing agent is added.

These deteriorations are found to be prevented or minimized by adding the said stabilizing agent.

Said stabilizing reagent is remarkably effective when the stabilizing agent and the antibacterial component are in close contact. This means that very limited stabilization can be observed when a powdered alkali metal salt of a compound (I) and the powdered stabilizing agent are mixed mechanically.

Therefore, it is preferable for producing the said stable lyophilized preparation to make a mixed aqueous solution of the antibacterially active component and the stabilizing agent, and then the solution is cooled to freeze it and subjected to the lyophilization in a manner conventional per se in the art.

The above stated requirements for the dark blue violet color formation implies non-existence of prior art related to the prevention effect of this invention, as none of such compounds filling the said requirements has been extensively studied and reported in known literatures.

Also nothing has been reported on the preventing effect of sugar or sugar alcohol on the decarboxylation of phenylmalonyl side chain even in the penicillin or cephalosporin field and the decomposition to produce heterocyclic thiol from the 3-position of cephalosporin or 1-dethia-1-oxa-3-cephem compounds.

Usually, the said lyophilized preparation is produced with the tray lyophilization, spray lyophilization vial lyophilization or like conventional methods by cooling the said mixed solution at subzero temperature e.g. −5° to −80° C. to freeze and then drying the frozen material under high vacuum by subliming the water component contained originally in the solution as a solvent thus leaving objective stable preparation of the lyophilized antibacterial. Heat of sublimation may be compensated by mild outside heating.

Remarkable prevention of the coloration can be seen when 0.05 parts or more by weight of the stabilizing agent is used for every 1 part by weight of the antibacterial salt. To prevent the chemical decomposition, 0.1 to 1 part by weight of the stabilizing agent is mixed with every 1 part by weight of the antibacterial salt.

An excess amount of more than 1 part by weight of the stabilizing agent is also effective in preventing color but it adversely affects the chemical stability, i.e., it prompts but does not retard the said chemical decomposition of the antibacterial component salts. This observation suggests that the effect of the stabilizing agent on the color formation is apparently a different kind of reaction from that of the chemical stabilization.

Thus, good results are generally obtained when the amount of added stabilizing agent is 0.1 to 1 part by weight.

A preservable lyophilized preparation of this invention is useful for, e.g., intravenous or drip administration, because it is highly soluble in water and it can be made as a sterile product. The product is also suitable a bulk material to be stored for a long time.

The product is preferably be kept in a tightly stoppered container in a cold place, e.g., at lower than 10° C., protected from moisture or strong light preferably under an inert gas e.g. argon, nitrogen, carbon dioxide or the like.

The preparation according to this invention produced under sterile condition can be dissolved in a fluid for injection, e.g., distilled water, physiological saline, or the like, optionally containing a co-acting substance, conventional additive for injection, analgesic or the like, and administered intravenously or intramuscularly to combat sensitive bacterial infection.

FIG. 1 shows the exceeding stability of the preparation of an antibacterial compound (I) disodium salt (Ar=p-hydroxyphenyl, Het=1-methyl-5-tetrazolyl) as produced by the method of Example 1 disclosed in the following part of this specification, using mannitol as the stabilizing agent (open circle) in reference to the corresponding control preparation containing no mannitol (closed circle).

The axis of ordinate shows the remaining amount of Compound (I) salt in percent to the initial value. The percentage is approximately equal to that of the remaining anti-bacterial potency in percent to the initial as estimated from the minimal inhibitory concentration against *Escherichia coli* 7437 up to 2 years of storage at 25° C.

FIG. 2 shows the exceeding chemical stabilization of the preparation as produced by the method of Example 1 vide infra using mannitol as the stabilizing agent (open circle) in reference to the corresponding control preparation containing no mannitol (closed circle). The axis of ordinate shows the amount in percent of the decarboxylation product which can be found after storage up to 2 years at 25 C., but originally absent in the preparation as estimated by the high precision liquid chromatographic technique. It is clearly shown that mannitol significantly suppressed the deterioration.

The following Examples illustrate the embodiments of this invention. Abbreviations have conventional meanings. The percentage content of a compound is calculated from the determination using the high performance liquid chromatographic technique and calculated and compared with the corresponding initial value.

EXAMPLE 1

A solution of Compound (I) (Ar=p-hydroxyphenyl, Het=1-methyl-5-tetrazolyl) disodium salt (1.084 g) and mannitol (0.16 g) in distilled water for injection (3 ml) is poured into a vial and frozen at −35° C. Then water is sublimed from the frozen mass under high vacuum to leave a stable lyophilized vial preparation.

When kept at 50° C. for 4 weeks, a reference preparation without mannitol shows deep gray-violet or yellowish color development, while the stable product prepared as above gets no color. Further, the decarboxylation decreased to a half, showing 92.6% of the remaining Compound (I) disodium salt as compared to the value of 84.5% in the reference preparation after 6 months storage at 45 C. After the period, only slower decomposition is observable with the stabilized preparation. This product is dissolved in five parts by weight of physiological saline and administered intravenously twice a day to a patient suffering from the upper respiratory tract infection caused by sensitive *Staphylococcus aureus*.

EXAMPLE 2

By substituting mannitol (0.16 g) in Example 1 with xylitol (0.16 g) or glucose (0.16 g), a similar prevention of the color development, decarboxylation or decomposition is observed.

EXAMPLE 3

By substituting mannitol (0.16 g) in Example 1 with inositol (0.5 g) or fructose (0.5 g), a similar prevention of the color development, decarboxylation and decomposition is observed.

EXAMPLE 4

A solution of Compound (I) (Ar=p-hydroxyphenyl, Het=1,3,4-thiadiazol-2-yl) disodium salt (1.08 g) and sorbitol (0.16 g) in distilled water for injection (3 ml) is placed in a vial and cooled to freeze. Then water is sublimed from the frozen mass under high vacuum to leave a stable lyophilized vial preparation.

When kept at 50° C. for 4 weeks, a reference preparation without sorbitol develops deep gray-violet and yellowish color, while the stable product prepared as above shows a remarkable prevention of the coloration. Further, content of the decarboxylation product decreases remarkably showing remaining Compound (I) disodium salt of 90% as compared to 84.5% of the reference preparation after 6 months storage at room temperature. Storage for a longer period shows only a little further decomposition.

This product is dissolved in twenty parts by weight of physiological saline and dripped intravenously thrice a day to a patient suffering from urinary tract infection caused by sensitive *Pseudomonas aeruginosa*.

EXAMPLE 5

By substituting sorbitol (0.16 g) of Example 4 with fructose (0.2 g), xylitol (0.5 g) or mannitol (0.15 g), a similar prevention of the color development, decarboxylation and decomposition is observed.

EXAMPLE 6

A solution of Compound (I) (Ar=p-hydroxyphenyl, Het=2-methyl-1,3,4-thiadiazol-5-yl) disodium salt (1.09 g) and glucose (0.16 g) in distilled water for injection (4 ml) is placed in a vial and cooled to freeze. Water is then sublimed from the frozen mass under high vacuum to leave a stable lyophilized vial preparation.

When kept at 50° C. for 4 weeks, a reference preparation without glucose develops deep gray-violet color, while the stable product prepared as above gets suppressed coloration. Decarboxylation product content decreases apparently. The stability of the drug represented by indices in terms of remaining amount after 6 months is improved. No further decomposition is observed thereafter with the stable preparation.

This product is dissolved in four parts by weight of physiological saline, mixed with lidocain injection and administered intramuscularly to protect a yound child from gram-positive or negative bacterial infection during surgical operation.

EXAMPLE 7

By substituting glucose (0.16 g) of Example 6 with fructose (0.3 g), mannitol (0.3 g) or mannose (0.1 g), a similar prevention of the color development, decarboxylation and decomposition is observed.

EXAMPLE 8

A solution of Compound (I) (Ar=4-hydroxy-2-fluorophenyl, Het=2-methyl-1,3,4-thiadiazol-5-yl) disodium salt (100 g) and sorbitol (30 g) in distilled water for injection (250 ml) is placed on a tray for lyophilization and cooled to freeze. Then water is sublimed from the frozen mass under high vacuum to leave a stable lyophilized bulk preparation.

This product also shows the remarkable stability to color development, decarboxylation and decomposition as in the case of Example 4.

This product is placed in a 300 ml container filled with dry argon, stoppered tightly, and kept at 0° C. for 2 years in a dark place during which period only a very limited deterioration is observed. This can be redissolved in water for making injection available in clinical use or for making lyophilized vial preparations of various sizes.

EXAMPLE 9

A similar prevention of the color development, decarboxylation and decomposition is observed by substituting sorbitol (30 g) of Example 8 with glucose (15 g) or mannitol (25 g).

EXAMPLE 10

In a manner similar to the preceding Examples, a stable lyophilized preparation of Compound (I) disodium salt (latamoxef) is produced by using arabinose, dulcitol, fructose, glucose, inositol, maltose, mannitol, mannose, sorbitol, sorbose, xylitol or xylose as the stabilizing reagent to find a significant prevention of the color formation after storing at 40° C. for 5 months. Among the reagents, arabinose, fructose, mannitol, sorbitol, sorbose, xylitol and xylose are found excellent. Maltose showed a weak prevention. Table I shows that the listed sugars and sugar alcohols minimize the chemical deterioration and protect the drug from color formation.

TABLE 1
RESULT OF STABILITY TESTS

| No. | Additive (15% w/w) | Storage for 5 month, 40° C. | Compound (I) diNa salt (%) | Decarboxy compound (%) | Prevent color |
|---|---|---|---|---|---|
| 1 | dulcitol | initial | 100.00 | 0.75 | ++ |
|   |          | after   | 88.41  | 4.46 |    |
| 2 | inositol | initial | 100.00 | 0.83 | ++ |
|   |          | after   | 91.34  | 4.31 |    |
| 3 | mannitol | initial | 100.00 | 0.73 | +++ |
|   |          | after   | 89.62  | 3.82 |    |
| 4 | sorbitol | initial | 100.00 | 0.80 | +++ |
|   |          | after   | 89.42  | 3.59 |    |
| 5 | xylitol  | initial | 100.00 | 0.52 | +++ |
|   |          | after   | 88.86  | 3.76 |    |
| 6 | arabinose | initial | 100.00 | 0.62 | +++ |
|   |           | after   | 90.59  | 2.98 |    |
| 7 | fructose | initial | 100.00 | 0.52 | +++ |
|   |          | after   | 91.94  | 3.40 |    |
| 8 | glucose  | initial | 100.00 | 0.63 | ++ |
|   |          | after   | 92.81  | 3.67 |    |
| 9 | maltose  | initial | 100.00 | 1.02 | ≠ |
|   |          | after   | 89.94  | 4.83 | − |
| 10 | mannose | initial | 100.00 | 0.66 | ++ |
|    |         | after   | 92.40  | 3.44 |    |
| 11 | sorbose | initial | 100.00 | 0.58 | +++ |
|    |         | after   | 91.83  | 3.35 |    |
| 12 | xylose  | initial | 100.00 | 0.94 | +++ |
|    |         | after   | 90.98  | 3.17 |    |
| /  | none (control) | initial | 100.00 | 1.21 | − |
|    |         | after   | 87.12  | 5.69 |    |

Note:
1. Contents (%) of the disodium salt and decarboxylation product are determined by the high performance liquid chromatography.
2. Column of "Prevent color" shows the effect of the additive stabilizing agent: +++ excellent; ++ moderate; ± fair; − poor.

What we claim is:

1. A stable lyophilized antibacterial preparation containing an alkali metal salt of 7β-(α-carboxy-α-arylacetamido)-7α-methoxy-3-heterocyclic thiomethyl-1-dethia-1-oxa-3-cephem-4-carboxylic acid of the formula $$\text{ArCHCONH} \begin{array}{c} \text{OCH}_3 \\ | \\ \text{COOH} \end{array} \text{(I)}$$

wherein Ar is a p-hydroxyphenyl group which is unsubstituted or substituted by halogen, hydroxy, 1 to 3 C alkoxy or 1 to 3 C alkyl, and Het is a 5 to 6 membered monocyclic heterocyclic group having 3 or 4 heteroatoms selected from nitrogen, oxygen or sulfur which is unsubstituted or is substituted by 1 to 5 C alkyl as antibacterial component and 0.1 to 1.0 part per part by weight antibacterial component of a sugar or sugar alcohol compound selected from arabitol, dambonitrol, dulcitol, inositol, mannitol, ononitol, pinitol, quercitol, sequoytol, sorbitol, viburnitol, xylitol, allose, altrose, arabinose, fructose, galactose, glucose, gulose, idose, lactose, lyxose, maltose, mannose, ribose, ribulose, sedoheptulose, sorbose, sucrose, tagatose, talose and xylose as stabilizing agent for the purpose of preventing blue color formation.

2. A preparation claimed in claim 1 in which the Ar group of the antibacterial component is p-hydroxyphenyl or 4-hydroxy-2-fluorophenyl.

3. A preparation claimed in claim 1 in which the Het group of the antibacterial component is unsubstituted or has methyl, ethyl or isobutyl as the substituent.

4. A preparation claimed in claim 1 in which the Het group of the antibacterial component is selected from 1,2,3-triazol-4-yl, 1-methyl-5-tetrazolyl, 1,3,4-thiadiazol-2-yl and 2-methyl-1,3,4-thiadiazol-5-yl.

5. A preparation claimed in claim 1 in which the alkali metal salt is a lithium, sodium or potassium salt.

6. A preparation claimed in claim 1 in which the antibacterial component is a mixture of one or more kinds of the alkali metal salts.

7. A preparation claimed in claim 1 in which the sugar alcohol has 6 carbon atoms.

8. A preparation claimed in claim 1 in which the sugar alcohol or sugar is selected from mannitol, sorbitol, xylitol, arabinose, fructose, sorbose and xylose.

9. A preparation claimed in claim 1 in which the sugar alcohol or sugar is selected from dulcitol, inositol, glucose, and mannose.

10. A preparation claimed in claim 1 that contains mannitol as the sugar alcohol.

11. A preparation claimed in claim 1 which is prepared by freeze drying of a mixed aqueous solution containing the antibacterial component and the stabilizing agent.

12. A preparation claimed in claim 1 that contains a sodium salt of 7β-(α-carboxy-α-p-hydroxyphenylacetamido)-7α-methoxy-3-(1-methyl-5-tetrazolyl)thiomethyl-1-dethia-1-oxa-3-cephem-4-carboxylic acid, 7β-(α-carboxy-α-p-hydroxyphenylacetamido)-7α-methoxy-b 3-(1,3,4-thiadiazol-2-yl)thiomethyl-1-dethia-1-oxa-3-cephem-4-carboxylic acid, 7β-(α-carboxy-α-p-hydroxyphenylacetamido)-7α-methoxy-3-(2-methyl-1,3,4-thiadiazol-5-yl)thiomethyl-1-dethia-1-oxa-3-cephem-4-carboxylicacid or 7β-(α-(4-hydroxy-2-fluorophenyl)-α-carboxyacetamido)-7α-methoxy-3-(2-methyl-1,3,4-thiadiazol-5-yl)thiomethyl-1-dethia-1-oxa-3-cephem-4-carboxylic acid.

13. A preparation claimed in claim 1 in which the salt is a sodium or potassium salt.

14. A preparation claimed in claim 1 in which the salt is a mono-salt or di-salt.

15. A preparation claimed in claim 1 in which the antibacterial component is a mixture of the alkali metal salts.

16. A preparation claimed in claim 1 stored in an inert gas.

17. A method for the production of a lyophilized antibacterial preparation as defined in claim 1 which comprises (1) dissolving the antibacterial component and the stabilizing agent, said component and agent being as defined in claim 1, in an injectable aqueous carrier to obtain a mixed aqueous solution; (2) cooling the solution to freezing at subzero temperature and (3) subliming the water contained in the frozen mass to obtain a non-coloring table lyophilized preparation.

18. A method claimed in claim 17 wherein the freezing and subliming are carried out in a tray or vial.

19. A method claimed in claim 17 in which the Ar group of the antibacterial component is p-hydroxyphenyl or 4-hydroxy-2-fluorophenyl.

20. A method claimed in claim 17 in which the Het group of the antibacterial component is unsubstituted or has methyl, ethyl or isobutyl as the substituent.

21. A method claimed in claim 17 in which the Het group of the antibacterial component is selected from 1,2,3-triazol-4-yl, 1-methyl-5-tetrazolyl, 1,3,4-thiadiazol-2-yl and 2-methyl-1,3,4-thiadiazol-5-yl.

22. A method claimed in claim 17 in which the alkali metal salt is a lithium, sodium or potassium salt.

23. A method claimed in claim 17 in which the antibacterial component is a mixture of one or more kinds of the salts.

24. A method claimed in claim 17 in which the sugar alcohol has 6 carbon atoms.

25. A method claimed in claim 17 in which the sugar alcohol or sugar is selected from mannitol, sorbitol, xylitol, arabinose, fructose, sorbose and xylose.

26. A method claimed in claim 17 in which the sugar alcohol or sugar is selected from dulcitol, inositol, glucose and mannose.

27. A method claimed in claim 17 in which the sugar alcohol is mannitol.

* * * * *